United States Patent [19]

Barker et al.

[11] Patent Number: 5,468,638
[45] Date of Patent: Nov. 21, 1995

[54] CELL CULTURE INSERT

[75] Inventors: Susan Barker, Tenafly; I-Hsi Chu, West Orange; Oresta N. Fedun, Wanaque; Tadeusz A. Tyndorf, Manalapan, all of N.J.

[73] Assignee: Becton, Dickinson aand Company, Franklin Lakes, N.J.

[21] Appl. No.: 952,004

[22] Filed: Sep. 28, 1992

[51] Int. Cl.⁶ ..................................... C12M 3/06
[52] U.S. Cl. .................. 435/304.1; 435/297.1; 435/305.1; 435/289.1; 422/101
[58] Field of Search ..................... 422/101, 102, 422/104; 435/240–241, 284–286, 287, 296–301, 310, 311; 210/238

[56] References Cited

U.S. PATENT DOCUMENTS

| | | | |
|---|---|---|---|
| 2,677,646 | 5/1954 | Lovell et al. | 195/139 |
| 4,125,436 | 11/1978 | Liner | 195/127 |
| 4,246,339 | 1/1981 | Cole et al. | 435/7 |
| 4,308,351 | 12/1981 | Leighton et al. | 435/284 |
| 4,608,342 | 8/1986 | Nees | 435/240 |
| 4,670,396 | 6/1987 | Bear et al. | 435/285 |
| 4,686,190 | 8/1987 | Cramer et al. | 435/291 |
| 4,748,124 | 5/1988 | Vogler | 435/240 |
| 4,871,674 | 10/1989 | Matsui et al. | 435/284 |
| 4,917,793 | 4/1990 | Pitt et al. | 435/284 X |
| 4,975,377 | 12/1990 | Key | 422/102 X |
| 5,026,649 | 6/1991 | Lyman et al. | 435/284 |
| 5,215,920 | 6/1993 | Lyman et al. | 422/102 X |

FOREIGN PATENT DOCUMENTS

| | | |
|---|---|---|
| 0495213 | 12/1990 | European Pat. Off. . |
| 0505118 | 3/1991 | European Pat. Off. . |

Primary Examiner—Jeffrey R. Snay
Attorney, Agent, or Firm—Nanette S. Thomas

[57] ABSTRACT

Apparatus for growing tissue cultures in vitro, which permits a concentration gradient of nutrients to develop through a permeable membrane to which a sample of tissue is attached. The permeable membrane is attached to the bottom end of a cell culture insert that in turn is supported by a flange connected to its upper end on the top of a well containing the nutrients and is self centered in the well by the arrangement of the sidewalls of the cell culture insert. The self centering feature of the insert minimizes capillary action.

13 Claims, 5 Drawing Sheets

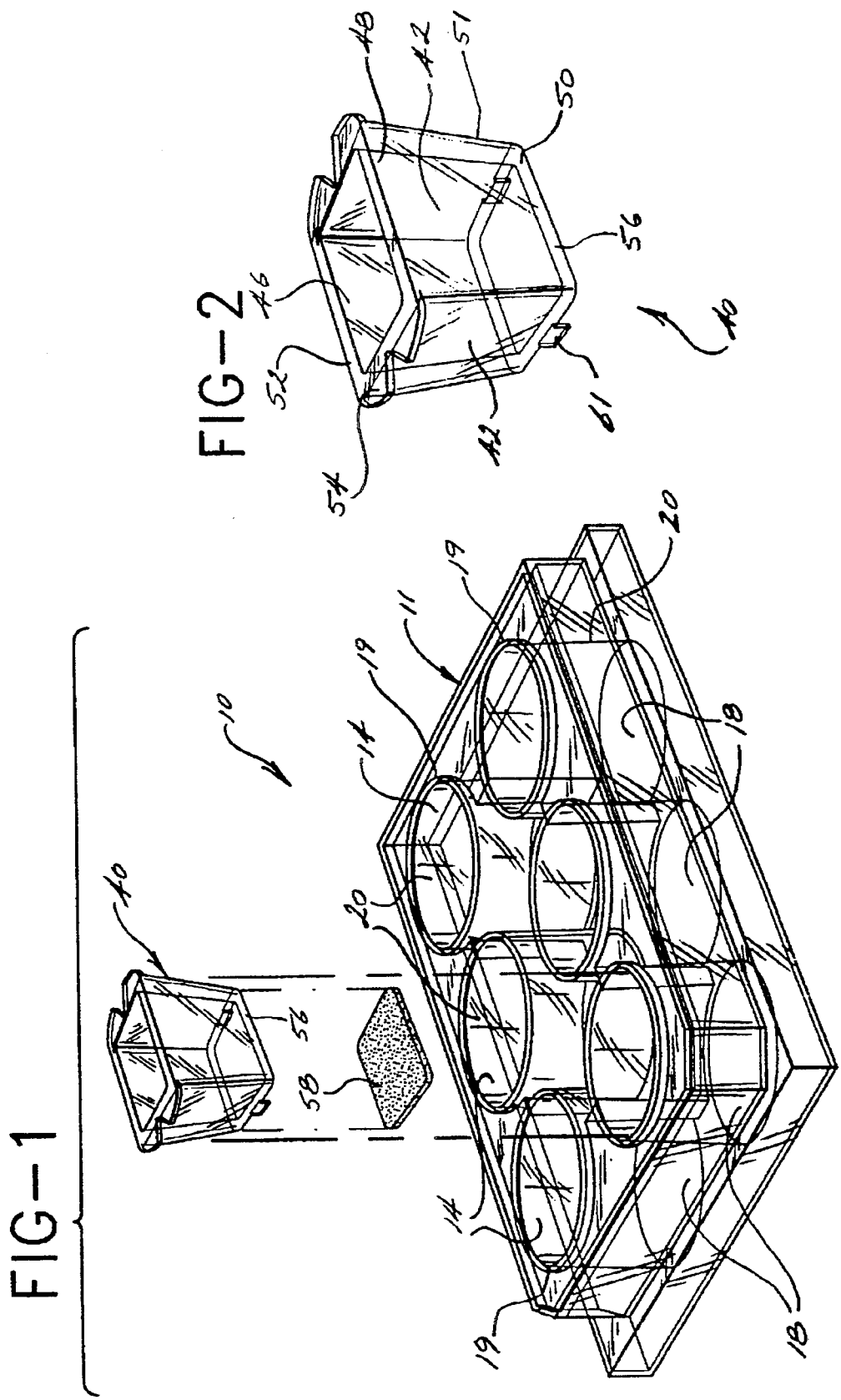

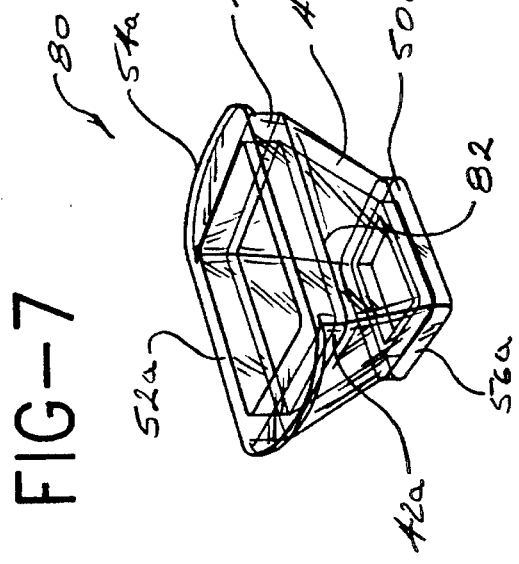
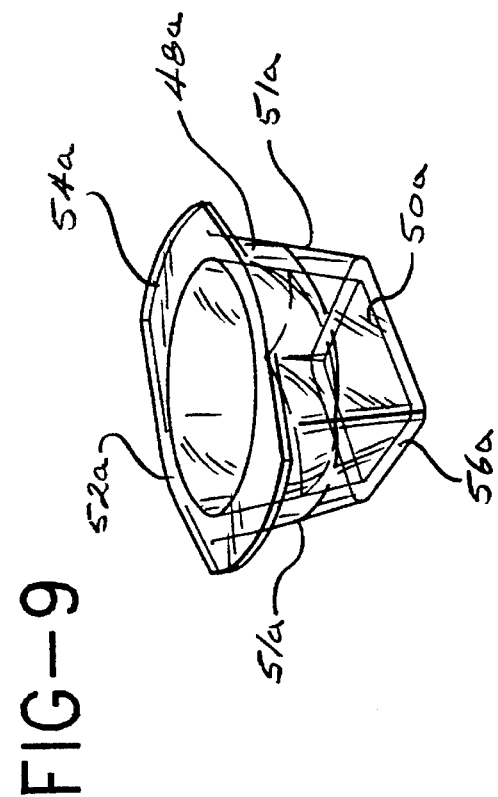
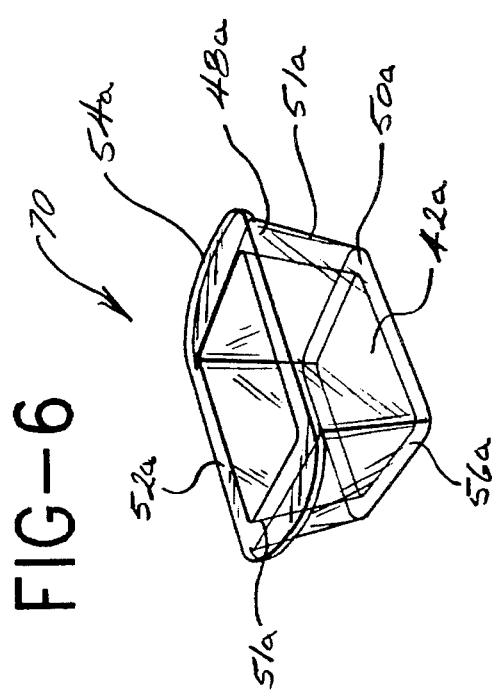
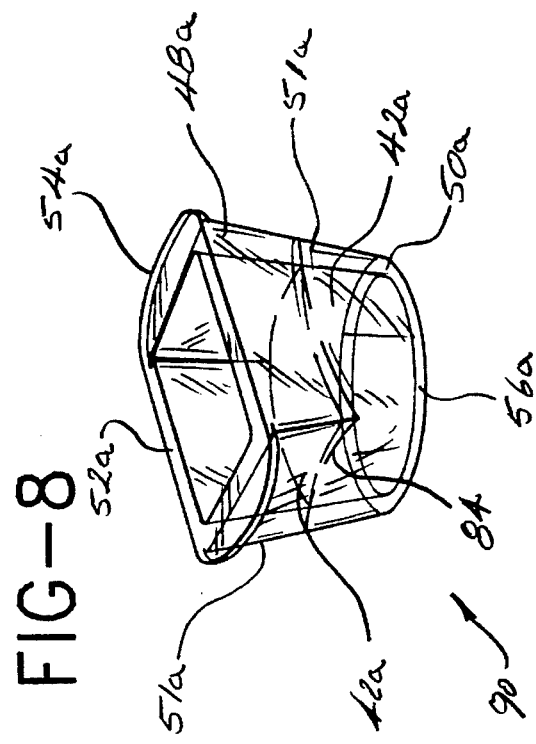

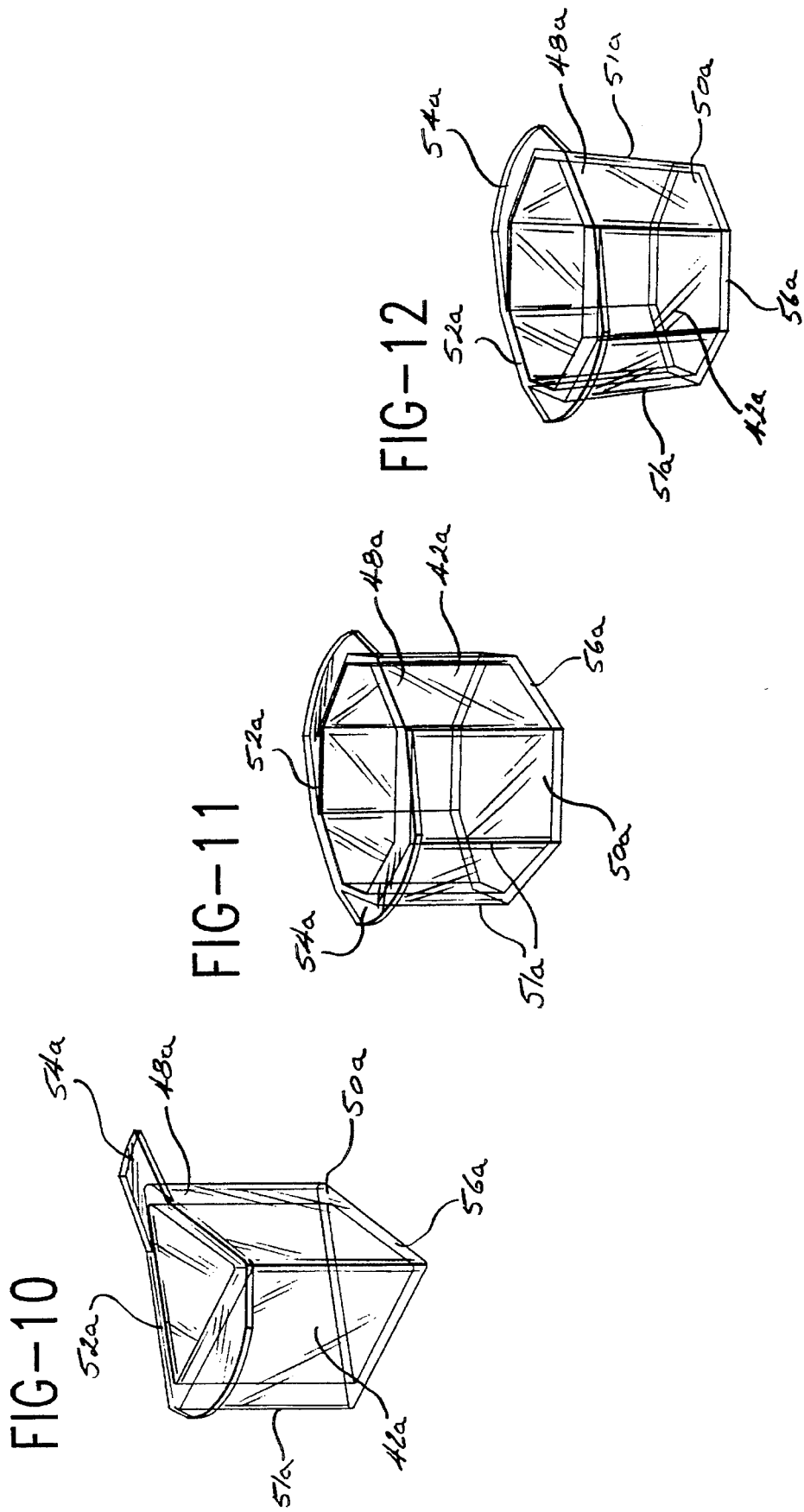

CELL CULTURE INSERT

BACKGROUND OF THE INVENTION

1. Field of the Invention

This invention relates to an apparatus for growing cells or tissue culture in vitro and more particularly comprises a new and improved cell culture insert for supporting tissue cultures in a fluid medium containing nutrients which promote the tissue culture growth.

2. Description of the Related Art

Cell culture inserts comprise a plastic material with a membrane on the bottom surface thereof so that there is free diffusion and transport of ions and macro-molecules. With the use of a suspended microporous membrane, two cell types, for example, can be cultured, one on each side of the membrane in the same well. Without suspension, cells on the bottom surface of the membrane would be exposed to damage. The microporous membrane allows free passage of macromolecules, proteins and ions. As a result, the interactions of the two cell types can be studied without actual physical contact between the two cell populations in the suspended state of the insert.

Conventional cell culture inserts and devices are described in U.S. Pat. Nos. 4,871,674 and 5,026,649. U.S. Pat. No. 4,871,674 discloses a culture cell which comprises discontinuous projecting parts for hanging the culture cell provided on an upper circumferential part and a membrane filter on the bottom. U.S. Pat. No. 5,026,649 discloses a culture cell which comprises a projecting part for hanging the culture cell which is provided over the whole upper circumferential part, with openings in the sidewall for exchanging gas and for pipeting sample.

In the use of these cell culture inserts, gases may not be exchanged sufficiently because the area of the openings is small. Furthermore, as described in U.S. Pat. No. 5,026,649, portions of the cell culture inserts could possibly become contaminated because the openings are provided in the sidewall of the cell culture insert.

SUMMARY OF THE INVENTION

The present invention is a cell culture insert comprising an upper portion, a lower portion and sidewalls extending from the upper portion to the lower portion. The lower portion includes a bottom surface which may have attached thereto a flat permeable membrane, a glass cover slip or the like. The upper portion includes a top surface which carries at least one outwardly extending flange which serves to support the insert in the well of a tissue culture vessel. The sidewalls are preferably arranged with respect to one another to form a geometric configuration such as a triangle, rectangle, square, hexagon, octagon and the like. The cell culture insert may be formed in different sizes and geometric configurations so as to be used with different sizes and geometric configured tissue culture vessels.

Preferably, the cell culture insert comprises four sidewall sections that taper from the upper portion to the lower portion and are arranged with respect to one another to form a geometric configuration wherein there are four corners. The corners provide means for self centering the cell culture insert when positioned for use in the tissue culture vessel that may have a well of a circular geometric configuration. The corners restrict the sidewalls from moving close to the well of the tissue culture vessel in which it is placed to minimize capillary action of fluid in the well. Furthermore, a piper may be inserted between the sidewalls of the cell culture insert and the well of the tissue culture vessel. The piper may be inserted without disturbing or removing the cell culture insert from the well to reach the bottom of the well of the tissue culture vessel and introduce or remove medium from beneath the membrane and about the outer surface of the cell culture insert without contaminating the upper surface of the membrane.

The exterior dimensions of the portion of the cell culture insert within the well are sufficiently less than the well interior diameter to allow a pipet or similar device to be positioned between the walls for fluid filling or aspiration.

Desirably, there are at least two outwardly extending flanges on the top end surface of the cell culture insert. These flanges may be spaced along the top end surface of the cell culture insert in a horizontal orientation so that when the cell culture insert is positioned in a tissue culture vessel, the flanges may rest on the top of the tissue culture vessel.

The flanges may also allow the cell culture insert to be supported in the tissue culture vessel so that there is a clearance between the bottom of the membrane and the bottom of the tissue culture vessel. The clearance provides a controlled static head and diffusion for the fluid in the tissue culture vessel so that cells can be properly cultured surfaces. The flange may also provide an area for gas exchange.

The cell culture insert may further comprise feet on the bottom end surface. The feet provide a degree of clearance between the membrane and the well bottom of the tissue culture vessel in the event the outwardly extending flange is not compatible with the tissue culture vessel and cannot support the cell culture insert. In addition, the feet may support the cell culture insert when placed on a surface.

An important feature of the cell culture insert of the present invention is the means for self centering. The sidewalls of the cell culture insert are restricted from moving close to the sidewall of the well of the tissue culture vessel in which it is placed so that capillary action of the fluid in the well is minimized.

DESCRIPTION OF THE DRAWINGS

FIG. 1 is an exploded perspective view of a conventional tissue culture vessel and the preferred cell culture insert of the present invention.

FIG. 2 is an enlarged perspective view of the preferred cell culture insert of the present invention without the membrane.

FIGS. 6, 7, 8, 9, 10, 11 and 12 are enlarged perspective views of alternate embodiments of the cell culture insert of the present invention without the membrane.

DETAILED DESCRIPTION

Figure 4:
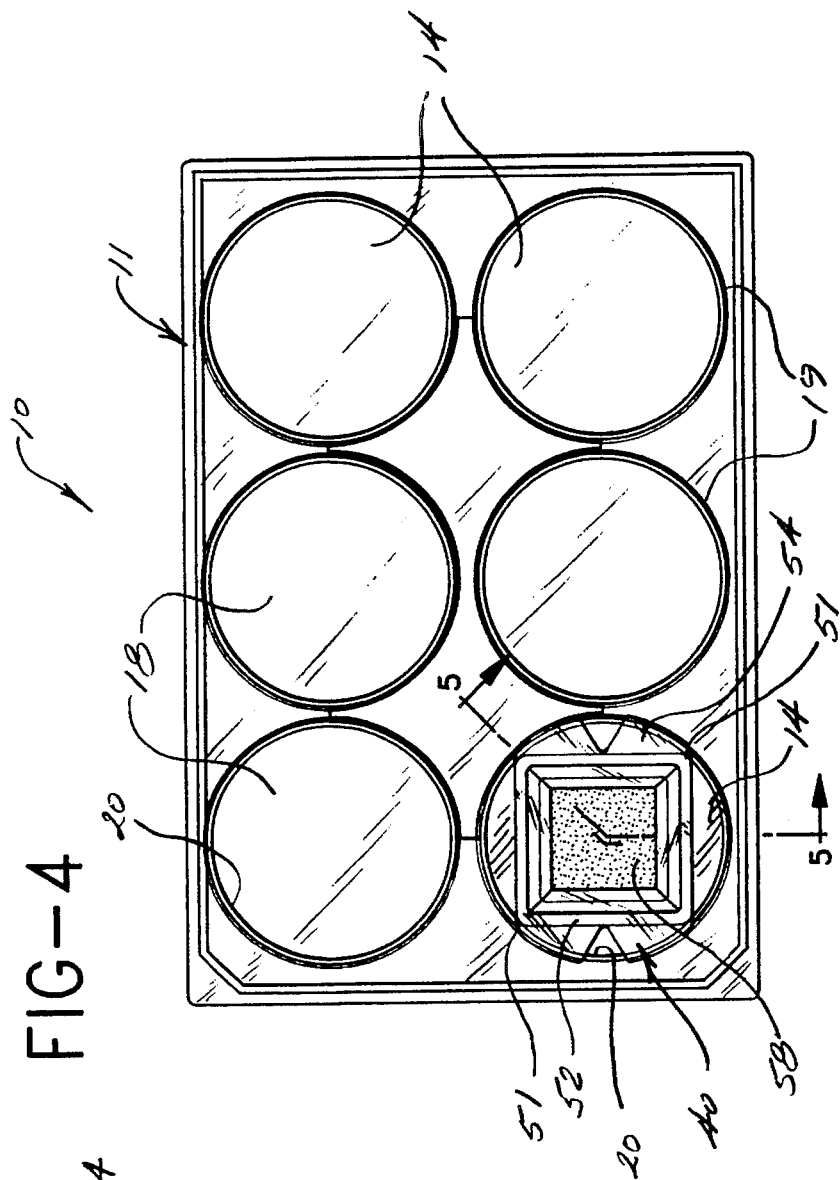
FIG. 4 is a top view of FIG. 1 illustrating the cell culture insert supported in the well of a tissue culture vessel.

The apparatus for growing tissue cultures as shown in FIG. 1 includes a tissue culture vessel 10 and a cell culture insert 40. Although only a six well tissue culture vessel is shown, it should be appreciated that the tissue culture vessel may have one, eight, twenty-four or some other number of wells selected for the particular purpose for which the apparatus is used.

Culture vessel 10 includes a base 11 comprising a number of wells 14 each comprising a sidewall 20 closed at the bottom by wall 18 and open at the top end 19. Base 11 is typically transparent and may be, for example, molded of polyvinylchloride.

While in the foregoing paragraphs the details of the culture vessel illustrated are described, it is to be appreciated that the vessel itself does not form part of the present invention, and the cell culture insert of the present invention may be sized to fit and be used with other culture vessels or like receptacles.

Figure 3:
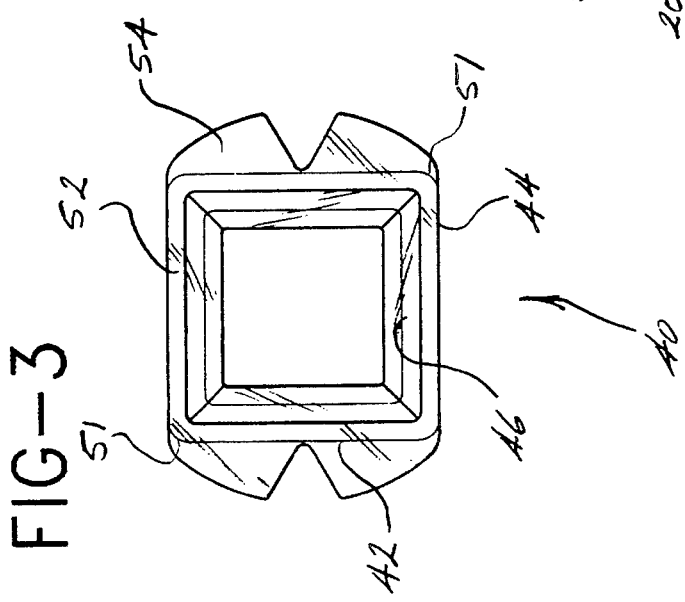
FIG. 3 is a top view of FIG. 2.

FIGS. 2 and 3 further illustrate cell culture insert 40 of the present invention comprising sidewalls 42 each having an outer surface 44 and a inner surface 46. The sidewalls taper from an upper portion 48 to a lower portion 50 wherein the outer circumference of upper portion 48 is greater than the outer circumference of lower portion 50.

The sidewalls are connected to one another at corners 51. The corners provide for self centering of the cell culture insert in the well, for substantially restricting the outer surface of the sidewalls from moving close to the well sidewalls so that capillary action of the fluid in the well is minimized and for allowing substantial movement of the insert within the well to facilitate pipet access.

Upper portion 48 comprises a top surface 52 which may carry an outwardly extending flange 54. Flange 54 provides a convenient grasping surface for the ready removal and placement of the cell culture insert into or out of the culture vessel as well as providing support to the cell culture insert when placed in the well of the culture vessel.

Lower portion 50 comprises a bottom surface 56 to which a microporous membrane 58 may be adhered. The membrane may be made of suitable material including, but not limited to, perforated inert film, hydrated gel, or a layered combination.

As shown in FIGS. 2, 3 and 4, when more than one outwardly extending flange 54 is used, they are spaced to allow for insertion of probes or pipers during the culturing procedure. The configuration of flange 54 may be structured to fit most situations. As shown, flange 54 may be formed with an opening for inserting a pipet or probe in the space between the cell culture insert and the well of the culture vessel. The flange configuration may facilitate the aseptic placement and removal of the cell culture insert into or out of the well of the culture vessel with tweezers or forceps, and allow for air circulation to minimize compartmentalization as well as providing support to the cell culture insert when placed in the well of a culture vessel.

It is most desirable that a space be maintained between the membrane on the bottom surface of the cell culture insert and the bottom of the well of the culture vessel so that cells may be cultured on both sides of the membrane. Therefore, the cell culture insert may further include feet 61 located on the bottom surface. Feet 61 may provide support to the cell culture insert in a particular culture vessel arrangement when the extending flanges are absent or are not compatible with a particular culture vessel arrangement. Feet 61 may further provide adequate support to the cell culture insert when it is removed from the culture vessel and rested on a surface.

Figure 5:
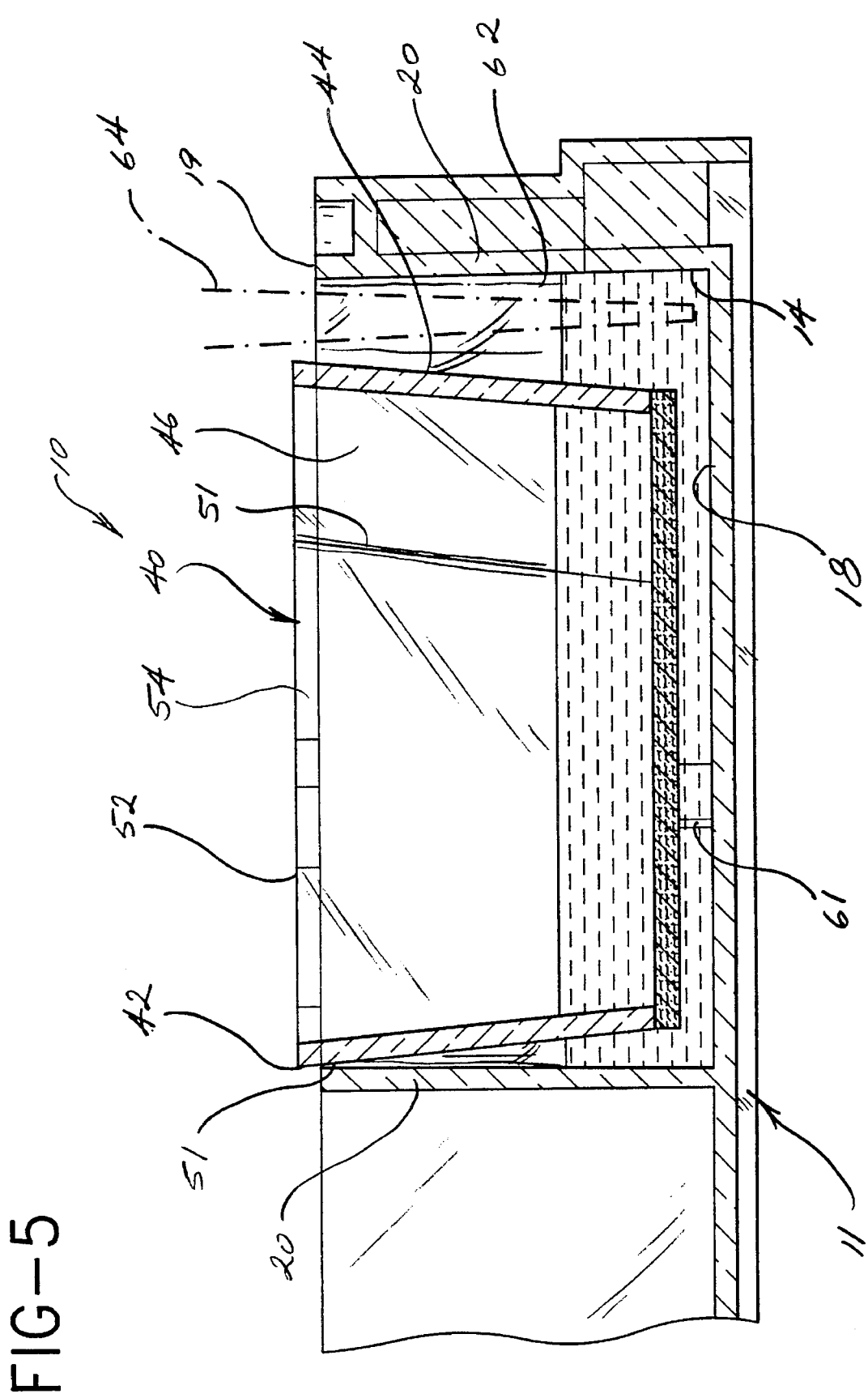
FIG. 5 is a cross-sectional view taken along lines 5—5 of FIG. 4 illustrating the self centering feature of the cell culture insert and where a pipet tip may enter the space between the sidewall of the cell culture insert and the well of the tissue culture vessel.

FIG. 5 illustrates the cell culture insert as supported by flanges 54 in a tissue culture vessel 10 and where a pipet tip 64 may enter the space between outer surface 44 of sidewalls 42 of the cell culture insert and sidewall 20 of well 14 of the culture vessel.

It will be appreciated that because of the self centering feature provided by corners 51, cell culture insert 40 is set within well 14 and spaced sufficiently from sidewall 20 of well 14 to minimize capillary action of solution or media in space 62 from wicking up outer surface 44 and entering the interior of the cell culture insert or from overflowing and spilling from well 14. Furthermore, while it is customary to position the membrane a distance above bottom 18 of the well of the culture vessel and since flange 54 supports the cell culture insert, the function of the cell culture insert may be carried out in a deeper well than suggested so as to provide more solution or media beneath the membrane or to provide additional space between the membrane and bottom 18.

FIGS. 6–12 show additional embodiments of the present invention which all allow for self centering of the cell culture insert when placed in the well of the culture vessel to minimize capillary action in the well. FIGS. 6–12 include many components which are substantially identical to the components of FIGS. 1–5. Accordingly, similar components performing similar functions will be numbered identically to those components of FIGS. 1–5, except that a suffix "a" will be used to identify those similar components in FIGS. 6–12.

FIG. 6 illustrates a cell culture insert 70 wherein the sidewalls extend from an upper portion 48a to a lower portion 50a and the outer circumference of upper portion 48a is substantially the same as the outer circumference of lower portion 50a.

The sidewalls are connected to one another at corners 51a. Corners 51a taper from upper portion 48a to lower portion 50a. The upper portion of the cell insert at the corners provide for self centering of the insert within a well, for substantially restricting the outer surface of the sidewalls from moving close to the well sidewalls and for allowing substantial movement of the cell culture insert within the well to facilitate piper access into the well.

Referring now to FIG. 7, an additional embodiment of the invention, culture cell insert 80 is shown comprising sidewalls 42a extend from upper portion 48a to a transitional portion 82 and then continue to extend to lower portion 50a. The outer circumference of lower portion 50a is less than the outer circumference of transitional portion 82 which is greater than the outer circumference of upper portion 48a. Corners 51a taper from transitional portion 82 to upper portion 48a and from transitional portion 82 to lower portion 50a. At the transitional portion of the cell culture insert, the corners provide for self centering of the insert within a vessel, for substantially restricting the outer surface of the sidewalls from moving close to the well sidewalls and for allowing substantial movement of the cell culture insert within the well to facilitate pipet access into the well.

Referring now to FIG. 8, yet a further embodiment of this invention, cell culture insert 90 is shown comprising sidewalls 42a which extend from upper portion 48a to a transitional portion 84 and then continue to a lower portion 50a. The outer circumference of lower portion 50a is less than the outer circumference of transitional portion 84 which is greater than the outer circumference of upper portion 48a. Corners 51a taper from transitional portion 84 to upper portion 48a and from transitional portion 84 to lower portion 50a.

Upper portion 48a comprises top surface 52a that is most preferably quadrangular in cross section. Lower portion 50a comprises bottom surface 56a that is most preferably circular in cross section.

An alternate embodiment of FIG. 8, is illustrated in FIG. 9 wherein top surface 52a that is most preferably circular in cross section and bottom surface 56a that is quadrangular in cross section.

FIGS. 10–12 further illustrate the alternate embodiments of the cell culture insert wherein sidewalls 42a may form different geometric configurations. FIG. 12 also illustrates that the sidewalls may be tapered from upper portion 48a to lower portion 50a.

As practitioners-in-the-art will understand, the cell inserts of the invention may be comprised of simple moldable parts which may be mass produced from a variety of materials, including, for example, polyethylene, polystyrene, polyethylene terephthalate, and polypropylene. As will be understood further by practitioners in the art, materials should be selected which provide a small degree of resiliency for the purpose of providing ease of insertion of the inserts of the invention into multi-well plates and ease of use for subsequent examination of the developed cultured cells. Such resiliency provides, also, for ease of adhering the membrane to the bottom surface of the cell culture insert.

What is claimed is:

1. A cell culture insert comprising:

a hollow chamber including an upper portion, a lower portion, sidewalls including an inner and outer surface extending from said upper portion to said lower portion and arranged with respect to one another to form at least three junctions, and a projecting flange extending radially outward from said upper portion beyond at least one sidewall, wherein said upper portion comprises an outer circumference and a top surface and sail lower portion comprises an outer circumference and a bottom surface, further comprising a transitional portion between said upper portion and said lower portion wherein said sidewalls extend from said upper portion to said transitional portion and from said transitional portion to said lower portion, wherein said outer circumference of said upper portion is substantially the same as said outer circumference of said lower portion, and wherein said transitional surface has an outer circumference substantially greater than said outer circumference substantially greater than said outer circumference of said upper portion and said outer circumference of said lower portion.

2. The insert of claim 1 further comprising means for supporting said insert extending from said bottom surface.

3. The insert of claim 1 wherein said sidewalls form a quadrangle.

4. The insert of claim 1 wherein each of said top surface and said bottom surface is a quadrangle.

5. The insert of claim 1 wherein each of said top surface and said bottom surface is a circle or an oval.

6. The insert of claim 1 wherein said top surface is a circle or an oval and said bottom surface is a quadrangle.

7. The insert of claim 1 wherein said top surface is a quadrangle and said bottom surface is a circle or an oval.

8. The insert of claim 1 wherein each of said top surface and said bottom surface is a quadrangle.

9. The insert of claim 1 wherein each of said top surface and said bottom surface is a circle or an oval.

10. The insert of claim 1 wherein said top surface is an oval and said bottom surface is a quadrangle.

11. The insert of claim 1 wherein said top surface is a quadrangle and said bottom surface is a circle or an oval.

12. The insert of claim 1 wherein said sidewalls taper from said transitional portion to said upper portion.

13. The insert of claim 12 wherein said sidewalls taper from said transitional portion to said lower portion.

* * * * *